(12) United States Patent
De Brabander et al.

(10) Patent No.: US 7,407,286 B2
(45) Date of Patent: Aug. 5, 2008

(54) DEVICE AND METHOD FOR PERFORMING MEASUREMENTS OF THE CHEMICAL COMPOSITION OF THE ANTERIOR EYE

(75) Inventors: Johny De Brabander, Berg en Terblijt (NL); Franciscus Hermanus Maria Jongsma, Maastricht (NL)

(73) Assignee: Universiteit Maastricht, Maastricht (NL)

( * ) Notice: Subject to any disclaimer, the term of this patent is extended or adjusted under 35 U.S.C. 154(b) by 0 days.

(21) Appl. No.: 10/555,436

(22) PCT Filed: Apr. 5, 2004

(86) PCT No.: PCT/EP2004/003679

§ 371 (c)(1),
(2), (4) Date: Jan. 18, 2007

(87) PCT Pub. No.: WO2004/098397

PCT Pub. Date: Nov. 18, 2004

(65) Prior Publication Data

US 2007/0127014 A1    Jun. 7, 2007

(30) Foreign Application Priority Data

May 5, 2003 (EP) .................................. 03076374

(51) Int. Cl.
*A61B 3/14* (2006.01)
*A61B 3/10* (2006.01)
*A61B 3/00* (2006.01)

(52) U.S. Cl. ...................... 351/206; 351/205; 351/221; 351/246

(58) Field of Classification Search .......... 351/200–246
See application file for complete search history.

(56) References Cited

U.S. PATENT DOCUMENTS

| 4,007,980 | A | * | 2/1977 | Bracher et al. | 351/219 |
| 4,176,920 | A | | 12/1979 | Ito | 351/207 |
| 4,728,183 | A | * | 3/1988 | Heacock et al. | 351/219 |
| 5,046,836 | A | * | 9/1991 | Volk | 351/219 |
| 5,252,998 | A | | 10/1993 | Reis et al. | 351/160 R |
| 5,523,810 | A | | 6/1996 | Volk | 351/219 |
| 5,973,779 | A | | 10/1999 | Suh et al. | 356/301 |
| 7,001,020 | B2 | * | 2/2006 | Yancey et al. | 351/221 |

* cited by examiner

*Primary Examiner*—Mohammed Hasan
(74) *Attorney, Agent, or Firm*—Birch, Stewart, Kolasch & Birch, LLP

(57) ABSTRACT

A device for determining a chemical composition of a living eye including a light emitting unit configured to emit a light beam, a light guidance unit including at least one first focusing lens having an entry surface and an exit surface to be brought in optical contact with the eye and to illuminate at least part of the eye with the light beam emitted by the light emitting unit and to receive and guide at least a fraction of a light beam leaving the eye towards the light detecting unit. The light guidance unit is arranged to illuminate the part of the eye with the light beam having an oblique angle of incidence with respect to a visual axis of the eye, and includes a second focusing lens having an entry surface and an exit surface. Further, the exit surface of the first focusing lens has a curvature conformal to a wave front of the light beam leaving the exit surface and impinging on the part of the eye.

26 Claims, 2 Drawing Sheets

US 7,407,286 B2

DEVICE AND METHOD FOR PERFORMING MEASUREMENTS OF THE CHEMICAL COMPOSITION OF THE ANTERIOR EYE

FIELD OF THE INVENTION

The present invention relates to a device for determining the chemical composition of a living eye comprising light emitting means, light guidance means comprising at least one first focussing lens having an entry surface and an exit surface to be brought in optical contact with the eye for illuminating at least part of said eye with a light beam emitted by said light emitting means and for receiving and guiding at least a fraction of the light beam leaving the eye as a result of said illumination towards light detecting means for determining the chemical composition of said eye by analysing said fraction of light and wherein said light guidance means are arranged for illuminating said part of the eye with a light beam having an oblique angle of incidence with respect to the visual axis of the eye.

The invention also relates to a method for determining the chemical composition of a living eye using a device according to anyone of the preceding claims, wherein light guiding means are brought in optical contact with the eye for illuminating at least a part of said eye with a light beam having an oblique angle of incidence with respect to the visual axis of the eye, wherein at least a fraction of light beam leaving the eye as a result of said illumination is received and guided towards sensing means and wherein the chemical composition of the eye is determined by analysis of said fraction of light.

BACKGROUND OF THE INVENTION

Many industrial, scientific and medical processes involve the measurement of the chemical composition of tissue of the human body for a variety of applications. In most cases the accuracy of the measurements is of great importance for the quality of the output of the process mentioned. A specific type of tissue measurements involve the measurement of the transparent media of the eye, as is applied, for example, in ophthalmology where proteins, pharmacological substances, or other molecules in aqueous humor are determined, wherein the presence of these substances provide an indication of the quality of the eye and sometimes information concerning underlying diseases.

Most methods of measuring the pathologic conditions in the eye are based on chemical and histological techniques to acquire information on molecule changes in the tissue or identification of pathogens which implies the use of spectroscopic techniques like absorption, scattering, electronic spin, and/or mass spectroscopy.

The limitations of these methods are that the most of them are performed in vitro, which makes invasive procedures in the eye necessary that may led to complications like hypotony or an endophthalmitus of the eye and is a frightening intervention from the patients point of view.

A solution is the application of in vivo spectroscopy, especially with Raman spectroscopy. Raman spectroscopy offers an opportunity to detect molecules qualitative as well quantitative and is a valuable tool to investigate biological materials in aqueous environments. For Raman spectroscopy in the living eye a laser beam is focussed in the tissue of interest and the back scattered light comprising the Raman signals is gathered, e.g. in a confocal device, and analyzed in a spectrometer.

The limitation of these methods is the restriction of the amount of incident light due to the vulnerability of the retinal tissue for light exposure, making the detection of molecules that are present in low concentration difficult if not impossible.

A solution is the application of an oblique illumination with respect to the visual axis of the eye in such a way that the incident excitation beam is not aimed at the retinal tissue. An oblique illumination of the eye can be performed with a device according to the preamble above.

A disadvantage of this technique is that the oblique alignment with the corneal surface interferes with the optical quality of the setup in such a way that it obstructs the confocal tissue selection.

SUMMARY OF THE INVENTION

It is an object of the present invention to provide a device and method according to the preamble above for performing measurements of the chemical composition or scattering properties of the tissues in the anterior eye, such as the cornea, the aqueous humor, or the anterior part of the lens, without interference of signals coming from adjacent tissue, and wherein the measurements can be performed in a noninvasive way.

It is an additional object of the present invention to provide a device and method according to the preamble above for performing measurements of the chemical composition of tissues or scattering properties with a real time integration length control, for monitoring changes in ocular tissue or in situ biomaterials, and for monitoring ocular pharmacokinetics.

These and other objects and advantages of the present invention are met as according to the invention said light guidance means comprises a further focussing lens having an entry surface and an exit surface, wherein said exit surface has a curvature conformal to the wave front of the light beam leaving said exit surface and impinging on said part of said eye.

With these features it is avoided that the light beam that impinges on the eye under an oblique angle of incidence with respect to the visual axis of the eye is directed or aimed at the fragile, retinal tissue, thus significantly limiting radiation damage to this fragile tissue due to illumination. Furthermore undesired refraction of light when entering the eye is also avoided, which undesired refraction normally will adversely affect the accuracy of the measurements. Hence with the device according to the present invention also undesired light refractional or interference phenomenon are avoided improving the accuracy of the measurements.

More in particular said entry surface of said further focussing lens has a curvature conformal to the wave front of the light beam leaving said exit surface of said first focussing lens and impinging on said entry surface of said further focussing lens. These features further ensures an undisturbed (e.g. without undesired refraction or interference) propagation of the light beam through the light guidance means before impinging on the eye, thus further enhancing the accuracy and speed of the measurements to be performed.

In a specific embodiment said further focussing lens comprises at least one internal mirror for reflecting said light beam towards said exit surface of said further focussing lens, wherein said further focussing lens comprises at least a second internal mirror for reflecting said light beam from said entry surface of said further focussing lens towards said first internal mirror. This embodiment allows a compact and efficient construction of the probe device with reduced constructional dimensions allowing an easy handling and positioning near the eye to be examined.

Furthermore with the use of internal mirrors the light beam is not adversely affected during its propagation through the probe device resulting in an illumination of the eye with a light beam having optimal optical properties, like intensity etc.

More in particular said first and/or said second internal mirror are conically shaped with respect to the visual axis of the eye, wherein during use the incident light beam passes said entry and exit surfaces of said further focussing lens perpendicular. These features further limit any undesired refraction at the different transition boundaries (air-lens and lens-air).

In another embodiment said entry and exit surfaces of said further focussing lens are spherically shaped.

In another embodiment said first internal mirror has a torical surface to correct the spherical aberration of said first focussing lens.

A further embodiment of the device according to the invention is characterized in that said further focussing lens comprises a conically shaped air-filled cavity surrounded by said second internal mirror.

More in particular said further focussing lens is symmetrically shaped and positioned with respect to the visual axis of the eye. This allows a compact construction which is easy to be handled by the personnel performing the measurements to the eye.

In another embodiment said further focussing lens is asymmetrically shaped with respect to the visual axis of the eye. These features allow an asymmetrically construction of the probe device Said light detecting means may comprise a spectrometer with a sensor such as a charge coupled device (CCD) or such as a photo multiplier.

As already stated a probe device according to the invention is provided with a further focussing lens in conjunction with an optical contact probe in which light rays of the incident excitation beam passes the curved boundaries of said contact probe perpendicular.

The advantage of such a configuration is that among others a perfect match on the index of refraction of the cornea can be obtained, especially by using a suitable contact fluid between the eye and said further focussing lens, such as for instance methylcellulose, making an undisturbed focus in the area of interest possible.

In another embodiment a positive collecting lens in conjunction with a contact probe of which all light transmitting surfaces, that are not meant to refract the light, are spherical shaped with a radius of curvature corresponding with the curvature of the incident convergent beam, guides the beam to the eye.

In a preferred embodiment the incident illumination beam is collected by a high aperture lens connected to a catadioptric contact probe consisting of a divergent axicon, that transforms the incoming convergent beam in an expanding circle shaped beam that is reflected by a conical internal mirror to a focal point on the optical axis of the high aperture lens. Said conical mirror has a torical surface to correct the spherical aberration of said high aperture lens.

In another embodiment of the invention, a contact probe is mounted on a high aperture lens and in the optical axis of this lens an excitation beam is focussed, that is guided by an auxiliary lens and said contact probe with internal flat mirror. The bow tie shaped excitation beam is imaged by the high aperture lens in conjunction with a tube lens on a for instance slit shaped fibre bundle light guide connected to a spectrometer or a photo multiplier. Volume of the measured tissue is controlled by the focal length of the high aperture lens and, real time, by a diaphragm placed in front of the slit shaped fibre bundle.

It will be appreciated that, in relation to spectroscopy of the living eye, the concept of using a contact probe of which the curved surfaces match the curvature of a focussed beam is widely applicable in a variety of cases, especially for medical purposes. Examples are infrared or Raman spectroscopy of the anterior tissues in the living eye or laser flare measurements of said tissues. However, these contact lenses lack optical compensation for the oblique boundary between lens and contact fluid that connects the lens with the corneal surface.

The above-mentioned and other features and advantages of the invention are illustrated in the following description of some embodiments of the present invention, with reference to the enclosed drawings. Systems arranged for deploying above-mentioned method are regarded as an embodiment of the present invention.

DETAILED DESCRIPTION OF THE EMBODIMENT

The present invention has three functions: focussing of a beam of excitation light in the eye in such a way that no direct light hits the retinal tissue, to preserve the optical quality of the excitation beam as is provided by the collection lens, and to collect, with a high aperture, the in the eye scattered light.

Figure 1:
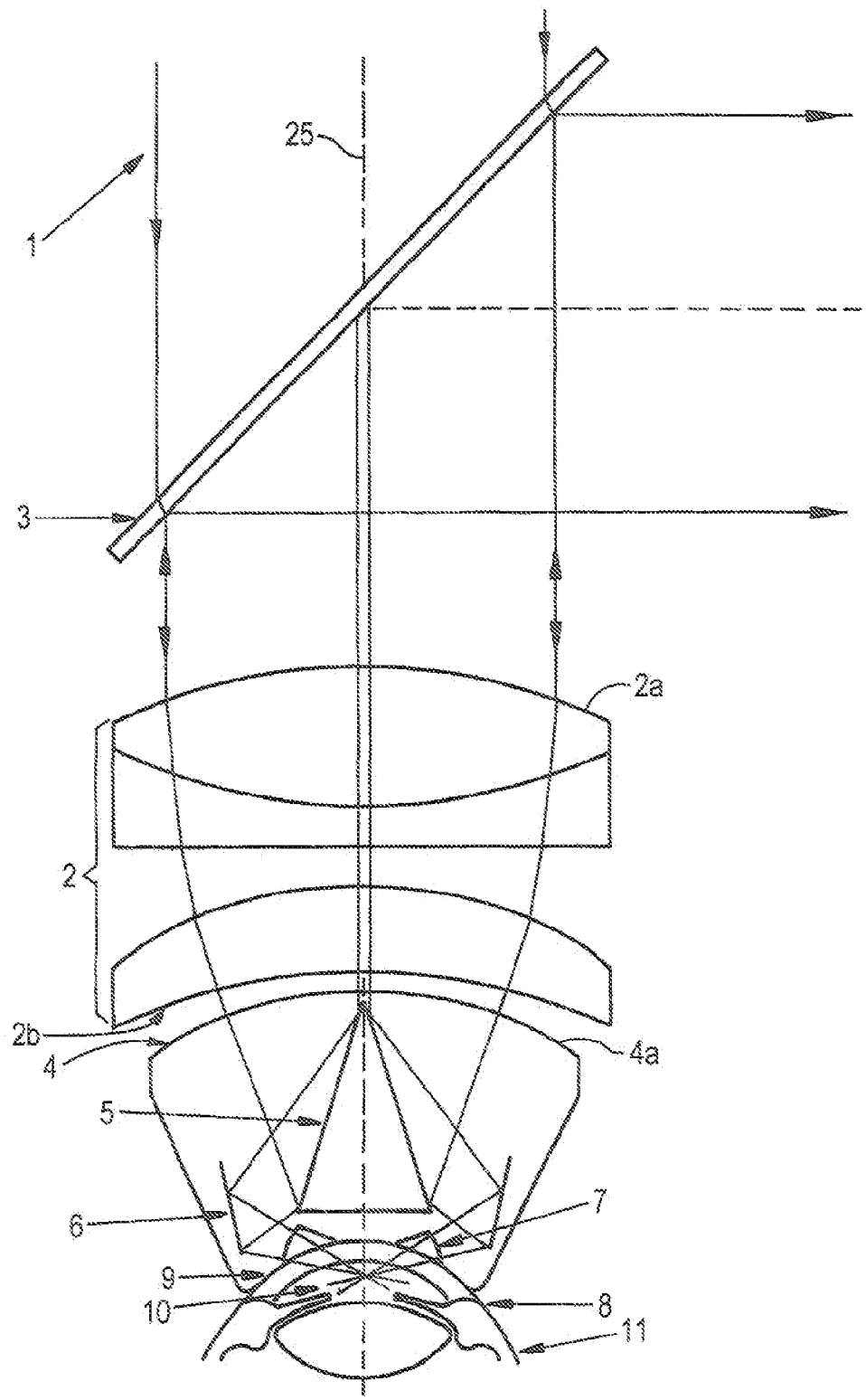
FIG. 1 shows a schematic cross section of a first embodiment of device according to the present invention allowing confocal probing in the eye.

A first embodiment of a device in which the present invention can be used is shown in FIG. 1.

The device of FIG. 1 has two main functions: to measure a spectral shift due to in-elastically scattered light or to measure the absorption bands (IR spectroscopy) or the intensity of the elastically scattered light (flare measurement).

Light emitting means (not shown), e.g. a laser emits an expanded laser beam 1. The laser beam 1 having a diameter equal to the front aperture of a first focussing lens 2 passes a dichroic beam-splitting mirror 3 and enters said first focussing lens 2 via its entry surface 2a. Near the back aperture or the exit surface 2b of said lens 2 a further focussing lens 4 acting as a contact probe guides the light into the eye 11. The entry surface 4a of said further focussing lens 4 is curved according the impinging wave front to avoid refraction due to the boundary air-lens surface.

The further focussing lens 4 is provided with an internal mirror 5 having a surface that is conical shaped with respect to the viewing axis 25 of the eye. This surface 5 forms an aberration-free divergent axicon. However, this internal mirror 5 reflects the light rather than to refract it as is common in axicons. The by said (second) mirror reflected light is directed to a further (first) conical mirror 6. Said conical mirror 6 has a torical surface to correct the spherical aberration of the first focussing lens 2.

The by the said first internal mirror 6 reflected light is directed to a circular shaped exit surface 7 having a curvature conformal to the impinging wave front to guide the light without refraction through the last boundary of the excitation part of the further focussing lens 4 into a film of contact fluid 8 present between the exit surface 7 of the further focussing lens 4 and the eye 11. As this contact fluid 8 has a refraction index that matches the corneal tissue 9, the light passes the outer corneal boundary without being refracted.

The beam is focussed in the aqueous humor 10 in such a way that no direct light enters the focussing lens 4 in case of Raman spectroscopy or flare measurement, but is allowed to re-enter the focussing lens 4 in case of IR absorption spectroscopy. The scattered light that enters the focussing lens 4 through the circular shaped exit surface 7 is guided backwards to the dichroic beam splitting mirror 3 and reflected to a sensor (not shown) being part of light detecting means.

The sensor can be for instance a spectrometer or a photomultiplier and serves to detect a fraction of light scattered back from the eye 11. The light detecting means are arranged for determining the chemical composition of said eye by analysing said fraction of light.

Figure 2:
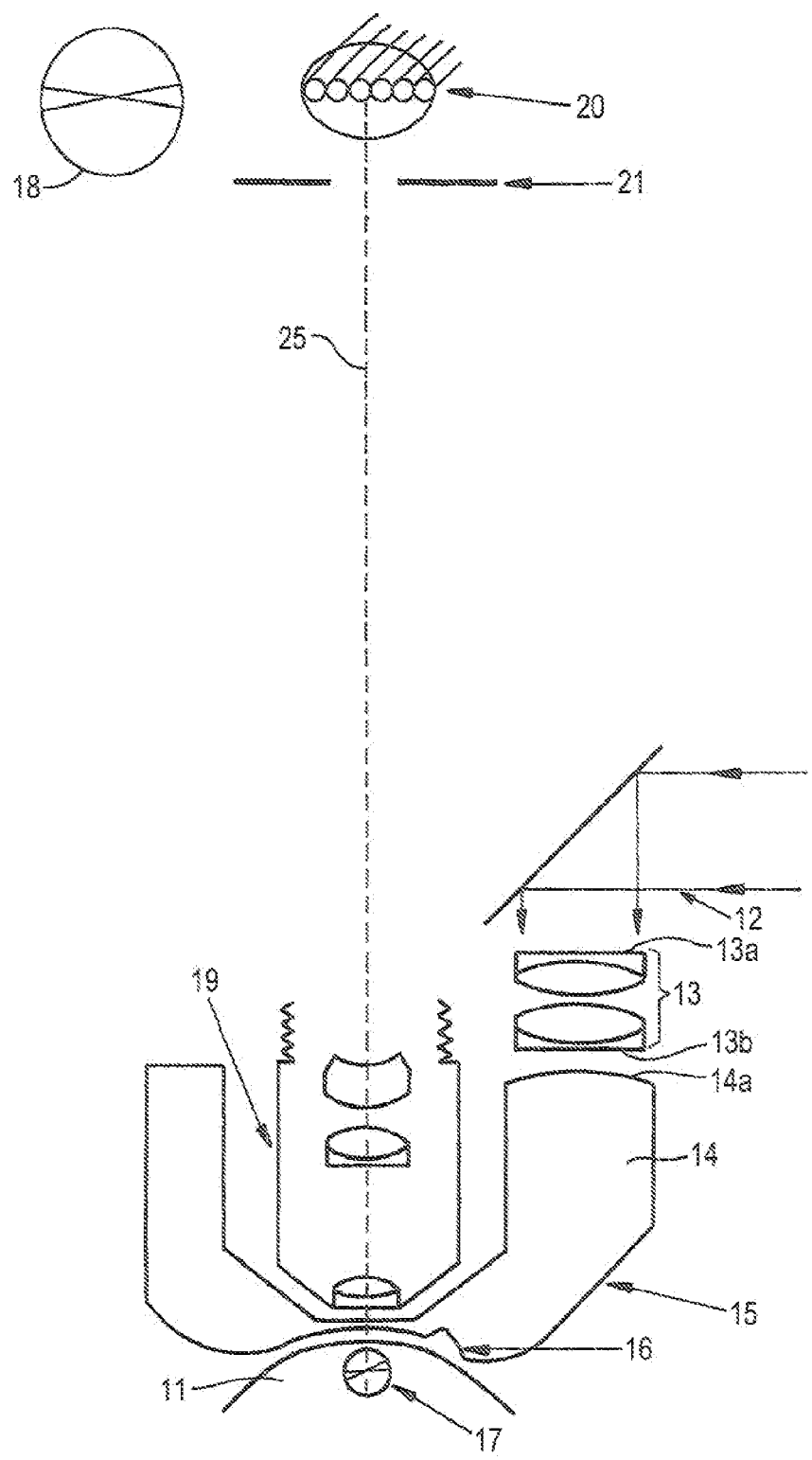
FIG. 2 shows a schematic cross section of another preferred embodiment of the invention in which optical dissection enables to probe the anterior eye.

In another embodiment of the invention the excitation light is fed into an optical dissection probe device, as shown in FIG. 2, that separates the incoming light spatially from the scattered light that is caught by a high aperture lens. An expanded laser beam 12 emitted by light emitting means, e.g. a laser (not shown) enters a first focussing lens 13 via its entry surface 13*a* and exits said first focussing lens 13 via its exit surface 13*b* towards the entry surface 14*a* of an asymmetric further focussing lens 14. This further focussing lens 14 acts as a contact probe to be positioned in optical contact with the eye 11 to be examined.

Said entry surface 14*a* of said further focussing lens 14 is spherical shaped with a curvature equal to the curvature of the impinging wave front leaving the first focussing lens 13. The light is further guided to a first internal mirror 15, that reflects the beam to the exit surface 16 of the further focussing lens 14. The exit surface 16 of the further focussing lens 14 has a curvature equal to the curvature of the wave front of the light beam impinging on the eye 11. Said impinging light beam is eventually focussed in, for instance, the aqueous humor 17 of the eye 11.

The back-scattered light from the bow tie shaped focussed light beam (see the cross section of the beam denoted in FIG. 2 with reference numeral 18) is imaged by a high aperture lens 19 on a fibre 20, that may have the shape of a slit to match the slit of a spectrometer.

The high aperture lens 19 having a finite image distance may be replaced by a for infinity corrected lens in conjunction with a tube lens to form an image, that matches the aperture of the exit fibre 20. The size of the image, and therefore the integration length in the anterior eye, can be controlled in real time with a field aperture 21.

The device and method according to the invention can also be used for measuring biomaterials in the anterior eye or for monitoring changes in the chemical composition of tissues or biomaterials. The device and method according to the invention are also suitable for monitoring ocular pharmacokinetics.

The invention claimed is:

1. A device for determining a chemical composition of a living eye, the device comprising:
    a light emitting unit configured to emit a light beam;
    a light guidance unit including at least one first focusing lens having an entry surface and an exit surface to be brought in optical contact with the eye to illuminate at least part of said eye with the light beam emitted by said light emitting unit and to receive and guide at least a fraction of a light beam leaving the eye towards the light detecting unit to determine the chemical composition of said eye by analyzing said fraction of light,
    wherein said light guidance unit is arranged to illuminate said part of the eye with the light beam having an oblique angle of incidence with respect to a visual axis of the eye,
    wherein said light guidance unit further includes a second focusing lens having an entry surface and an exit surface, and
    wherein said exit surface of the first focusing lens has a curvature conformal to a wave front of the light beam leaving said exit surface and impinging on said part of said eye.

2. The device according to claim 1, wherein said entry surface of said second focusing lens has a curvature conformal to the wave front of the light beam leaving said exit surface of said first focusing lens and impinging on said entry surface of said second focusing lens.

3. The device according to claim 1 or 2, wherein the second focusing lens comprises at least one internal mirror configured to reflect said light beam towards said exit surface of said second focusing lens.

4. The device according to claim 3, wherein the second focusing lens comprises at least a second internal mirror configured to reflect said light beam from said entry surface of said second focusing lens towards said first internal mirror.

5. The device according to claim 4, wherein at least one of said first and said second internal mirrors are conically shaped with respect to a visual axis of the eye.

6. The device according to claim 3, wherein said first internal mirror has a torical surface to correct a spherical aberration of said first focusing lens.

7. The device according to claim 1, wherein the incident light beam perpendicularly passes said entry and exit surfaces of said second focusing lens.

8. The device according to claim 1, wherein said entry and exit surfaces of said second focusing lens are spherically shaped.

9. The device according to claim 4, wherein said second focusing lens comprises a conically shaped air-filled cavity surrounded by said second internal mirror.

10. The device according to claim 1, wherein said second focusing lens is symmetrically shaped and positioned with respect to a visual axis of the eye.

11. The device according to claim 1, wherein the second focusing lens is asymmetrically shaped with respect to a visual axis of the eye.

12. The device according to claim 1, wherein said light detecting unit comprises a spectrometer with a sensor, and
    wherein the sensor comprises one of a charge coupled device (CCD) or photo multiplier.

13. The device according to claim 1, wherein a contact fluid is present between the eye and said second focusing lens, and
    wherein the contact fluid comprises methylcellulose.

14. A method for determining a chemical composition of a living eye, the method comprising:
    emitting a light beam via a light emitting unit;
    bringing a light guidance unit including at least one first focusing lens having an entry surface and an exit surface in optical contact with the eye, said light guidance unit being arranged to illuminate a part of the eye with the light beam having an oblique angle of incidence with respect to a visual axis of the eye, said light guidance unit further including a second focusing lens having an entry surface and an exit surface, and said exit surface of the first focusing lens having a curvature conformal to a wave front of the light beam leaving said exit surface and impinging on said part of said eye;

illuminating at least part of said eye with the light beam emitted by said light emitting unit;

receiving and guiding at least a fraction of a light beam leaving the eye towards the light detecting unit; and analyzing the received fraction of light to determine the chemical composition of said eye.

15. The method according to claim 14, wherein said entry surface of said second focusing lens has a curvature conformal to the wave front of the light beam leaving said exit surface of said first focusing lens and impinging on said entry surface of said second focusing lens.

16. The method according to claim 14, wherein the second focusing lens comprises at least one internal mirror configured to reflect said light beam towards said exit surface of said second focusing lens.

17. The method according to claim 16, wherein the second focusing lens comprises at least a second internal mirror configured to reflect said light beam from said entry surface of said second focusing lens towards said first internal mirror.

18. The method according to claim 17, wherein at least one of said first and said second internal mirrors are conically shaped with respect to a visual axis of the eye.

19. The method according to claim 17, wherein said second focusing lens comprises a conically shaped air-filled cavity surrounded by said second internal mirror.

20. The method according to claim 16, wherein said first internal mirror has a torical surface to correct a spherical aberration of said first focusing lens.

21. The method according to claim 14, wherein the incident light beam perpendicularly passes said entry and exit surfaces of said second focusing lens.

22. The method according to claim 14, wherein said entry and exit surfaces of said second focusing lens are spherically shaped.

23. The method according to claim 14, wherein said second focusing lens is symmetrically shaped and positioned with respect to a visual axis of the eye.

24. The method according to claim 14, wherein the second focusing lens is asymmetrically shaped with respect to a visual axis of the eye.

25. The method according to claim 14, wherein said light detecting unit comprises a spectrometer with a sensor, and
wherein the sensor comprises one of a charge coupled device (CCD) or a photo multiplier.

26. The method according to claim 14, further comprising: placing a contact fluid between the eye and said second focusing lens, and wherein the contact fluid comprises methylcellulose.

* * * * *